United States Patent
Nishizaka et al.

(10) Patent No.: US 12,263,392 B2
(45) Date of Patent: Apr. 1, 2025

(54) TRAINING DETERMINATION DEVICE, TRAINING DETERMINATION METHOD AND PROGRAM

(71) Applicant: CASIO COMPUTER CO., LTD., Tokyo (JP)

(72) Inventors: Nobuyoshi Nishizaka, Hamura (JP); Futoshi Yamamoto, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 872 days.

(21) Appl. No.: 17/415,658

(22) PCT Filed: Dec. 19, 2019

(86) PCT No.: PCT/JP2019/049898
§ 371 (c)(1),
(2) Date: Jun. 17, 2021

(87) PCT Pub. No.: WO2020/130089
PCT Pub. Date: Jun. 25, 2020

(65) Prior Publication Data
US 2022/0072401 A1 Mar. 10, 2022

(30) Foreign Application Priority Data
Dec. 19, 2018 (JP) .................................. 2018-237023

(51) Int. Cl.
*A63B 69/00* (2006.01)
*A63B 24/00* (2006.01)
*A63B 71/06* (2006.01)

(52) U.S. Cl.
CPC ...... *A63B 69/0028* (2013.01); *A63B 24/0006* (2013.01); *A63B 24/0062* (2013.01);
(Continued)

(58) Field of Classification Search
USPC ........................................................ 702/149
See application file for complete search history.

(56) References Cited

U.S. PATENT DOCUMENTS

| 8,568,277 B2 | 10/2013 | Johnson |
| 8,858,400 B2 | 10/2014 | Johnson |

(Continued)

FOREIGN PATENT DOCUMENTS

| JP | 2012-525220 A | 10/2012 |
| JP | 2012-228568 A | 11/2012 |

(Continued)

OTHER PUBLICATIONS

JPO; Application No. 2018-237023; Notice of Reasons for Refusal dated Feb. 24, 2021.
(Continued)

*Primary Examiner* — Paul D Lee
(74) *Attorney, Agent, or Firm* — Fitch, Even, Tabin & Flannery LLP (57) ABSTRACT

A training determination device includes: a determination unit configured to determine a training type, based on exercise data obtained when a user has performed a running training; a storage unit configured to store training history information in which the training type determined by the determination unit is associated with time information for performed training and a moving distance during the performed training; a calculation unit configured to perform at least two types of different calculation for a cumulative total of the moving distance for each training type, based on the training history information stored in the storage unit; and a display controller configured to display an image indicating the cumulative total of the moving distance for each training type calculated by the calculation unit.

18 Claims, 6 Drawing Sheets

(52) U.S. Cl.
CPC ...... *A63B 71/0622* (2013.01); *A63B 71/0686* (2013.01); *A63B 2024/0009* (2013.01); *A63B 2024/0068* (2013.01); *A63B 2024/0071* (2013.01); *A63B 2220/17* (2013.01); *A63B 2220/62* (2013.01)

(56) References Cited

U.S. PATENT DOCUMENTS

| | | |
|---|---|---|
| 2006/0217232 A1* | 9/2006 | Kondrat ............ A63B 69/0028 482/3 |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0233770 A1 | 9/2009 | Vincent et al. |
| 2010/0273610 A1 | 10/2010 | Johnson |
| 2012/0084054 A1* | 4/2012 | Yuen .................... A61B 5/0004 702/160 |
| 2012/0179278 A1 | 7/2012 | Riley et al. |
| 2012/0277040 A1 | 11/2012 | Vincent et al. |
| 2013/0173033 A1 | 7/2013 | Oleson et al. |
| 2014/0040266 A1 | 2/2014 | Johnson |
| 2014/0342329 A1 | 11/2014 | Debenedetto et al. |
| 2016/0213977 A1 | 7/2016 | Oleson et al. |
| 2016/0243403 A1 | 8/2016 | Oleson et al. |
| 2016/0245840 A1 | 8/2016 | Oleson et al. |
| 2017/0361156 A1* | 12/2017 | Sugiya ............... A63B 24/0075 |
| 2018/0001174 A1 | 1/2018 | Aoshima et al. |
| 2018/0043212 A1 | 2/2018 | Shirai et al. |
| 2018/0047194 A1 | 2/2018 | Shirai et al. |
| 2018/0253740 A1 | 9/2018 | Schmidt |
| 2018/0366025 A1 | 12/2018 | Dibenedetto et al. |
| 2020/0335006 A1 | 10/2020 | Dibenedetto et al. |

FOREIGN PATENT DOCUMENTS

| | | |
|---|---|---|
| JP | 2018000543 A | 1/2018 |
| JP | 2018-023680 A | 2/2018 |
| JP | 2018-023681 A | 2/2018 |
| JP | 2018-025517 A | 2/2018 |

OTHER PUBLICATIONS

Intellectual Property Office of India; Application No. 202117027103; Office Action dated Jun. 20, 2022.

EPO; Application No. 19897653.2; Office Action dated Jul. 20, 2023.

JPO; Application No. PCT/JP2019/049898; International Search Report and Written Opinion dated Mar. 17, 2020.

* cited by examiner

TRAINING DETERMINATION DEVICE, TRAINING DETERMINATION METHOD AND PROGRAM

CROSS-REFERENCE TO RELATED APPLICATIONS

This application is a U.S. national phase application filed under 35 U.S.C. § 371 of International Application No. PCT/JP2019/049898, filed Dec. 19, 2019, which is based upon and claims the benefit of priority from the prior Japanese Application No. 2018-237023, filed Dec. 19, 2018.

FIELD OF THE INVENTION

The present invention relates to a training determination device, a training determination method and a program for determining a type of running training.

BACKGROUND OF THE INVENTION

In the related art, disclosed is a training system configured to receive data from an exercise monitor for measuring performances of a speed, a pace, a distance and the like of a runner and to provide a user with a feedback including training information indicating whether the user meets a specific training standard based on the received data, during running (for example, refer to PTL 1).

CITATION LIST

Patent Literature

PTL 1: Japanese Unexamined Patent Application Publication No. 2012-228568

SUMMARY OF INVENTION

Technical Problem

In general, for example, in order to take part in a marathon race, the user should perform efficient training by combining different types of exercises.

However, the feedback that is provided by the training system disclosed in PTL 1 is not sufficient as information to efficiently perform training for a marathon race.

The present invention has been made in view of the above situations, and an object thereof is to provide a training determination device, a training determination method and a program for efficiently performing running training.

Solution to Problem

A training determination device related to one aspect includes: a determination unit configured to determine a training type, based on exercise data obtained when a user has performed a running training; a storage unit configured to store training history information in which the training type determined by the determination unit is associated with time information for performed training and a moving distance during the performed training; a calculation unit configured to perform at least two types of different calculation for a cumulative total of the moving distance for each training type, based on the training history information stored in the storage unit; and a display controller configured to display an image indicating the cumulative total of the moving distance for each training type calculated by the calculation unit.

According to the present invention, it is possible to efficiently perform the running training.

DESCRIPTION OF EMBODIMENTS

Hereinafter, an exemplary embodiment of the present invention will be described in detail with reference to the accompanying drawings. The present invention is not limited to the illustrated example.

Training Determination System

A configuration of the exemplary embodiment is described with reference to FIGS. 1 and 2.

First, a training determination system 1 of the exemplary embodiment is described with reference to FIG. 1.

Figure 1:
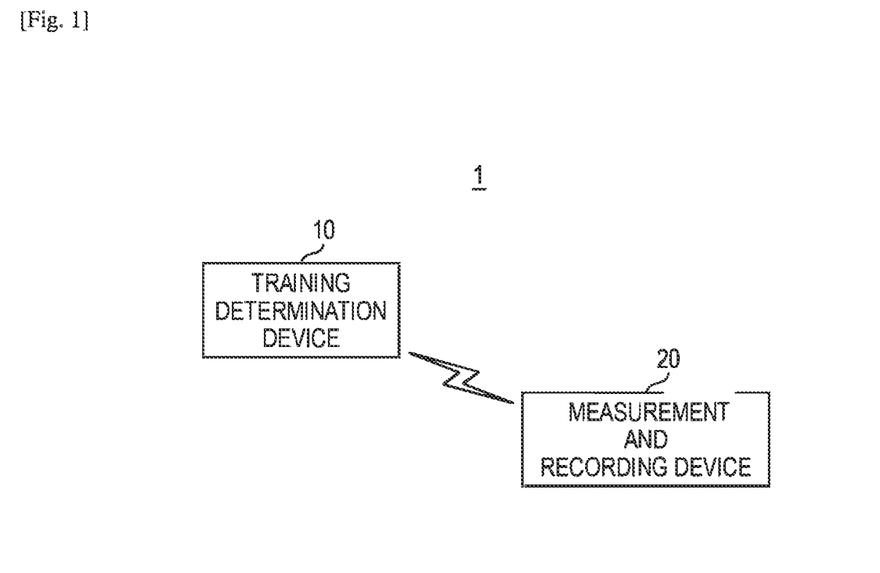
FIG. 1 is a block diagram depicting a training determination system in accordance with an exemplary embodiment of the present invention.
Figure 2:
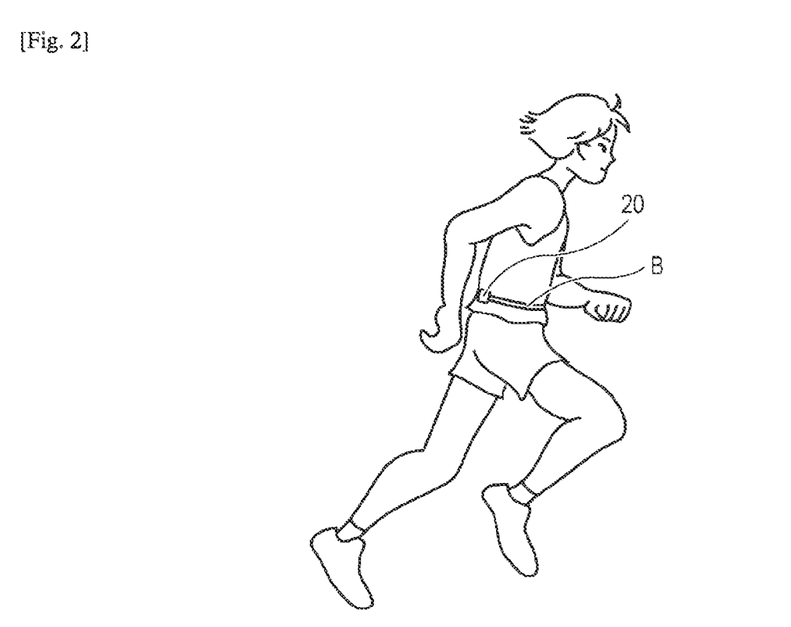
FIG. 2 illustrates a state in which a user wears a measurement and recording device.

FIG. 1 is a block diagram depicting the training determination system 1 of the exemplary embodiment. As shown in FIG. 1, the training determination system 1 includes a training determination device 10, and a measurement and recording device 20.

The training determination device 10 is a device configured to, when a user (subject) has performed running training (including a race), determine a training type by using exercise data (for example, information such as lap time and a running distance) of the user acquired from the measurement and recording device 20. Also, the training determination device 10 is a device configured to store a training type and a date and a running distance at the time when the training has been performed in association with each other whenever determining the training type, and to calculate and output a cumulative total of the running distances in each of the training types.

As the training determination device 10, a smart phone, a laptop PC (Personal Computer), a desktop PC, a tablet PC and the like may be exemplified, In the below, a case in which the training determination device 10 is a smart phone is described.

The measurement and recording device 20 is a device configured to be worn on the user during the running training (including a race) and to collect and record exercise data (for example, information such as lap time and a running distance) during the training. As shown in FIG. 2, the measurement and recording device 20 has an adjunctive belt B and is fixed in a position of the user's waist by the belt B, for example.

The measurement and recording device 20 may have a clip, instead of the belt B, and may be fixed in the position of the user's waist by pinching a running wear of the user with the clip.

Training Determination Device

Figure 3A:
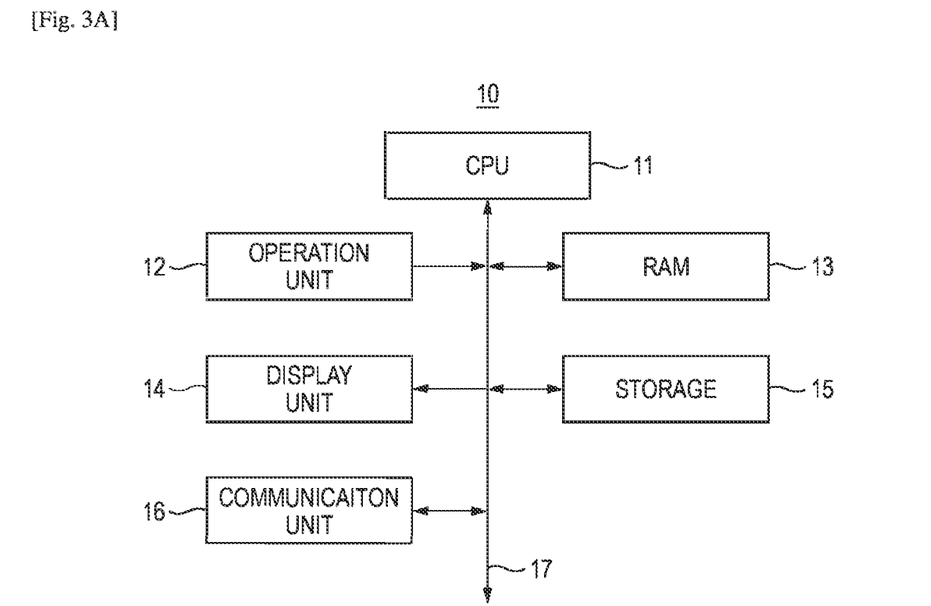
FIG. 3A is a block diagram depicting a functional configuration of a training determination device.

Subsequently, a functional configuration of the training determination device 10 is described with reference to FIG. 3A. FIG. 3A is a block diagram depicting a functional configuration of the training determination device 10.

The training determination device 10 includes a CPU (Central Processing Unit) 11, an operation unit 12, a RAM (Random Access Memory) 13, a display unit 14, a storage 15, and a communication unit 16. The respective units of the training determination device 10 are connected via a bus 17.

The CPU (an acquisition unit, a determination unit, a setting unit, a calculation unit, a time period designation nun, and a display controller) 11 is configured to control the respective units of the training determination device 10. The CPU 11 is configured to read a designated program of system programs and application programs stored in the storage 15, and to develop read program on the RAM 13, thereby executing a variety of processing in cooperation with the program.

The operation unit (a time period designation unit) 12 includes a touch panel, for example, and is configured to receive a touch input from the user and to output information about the operation to the CPU 11, for example.

The touch panel is integrated with the display unit 14, and is configured to detect XY coordinates of a user's touch position on the display unit 14 by a variety of methods such as an electrostatic capacitance method, a resistive film method, an ultrasonic surface acoustic wave method, and the like, for example, The touch panel is configured to output a position signal about the XY coordinates of the touch position to the CPU 11.

The RAM 13 is a volatile memory, and forms a work area in which diverse data and programs are temporarily stored.

The display unit (display unit) 14 is configured by an LCD (Liquid Crystal Display), an EL (Electro Luminescence) display or the like, and is configured to make diverse displays in accordance with display information instructed from the CPU 11.

The storage (storage unit) 15 is configured by a flash memory, an EEPROM (Electrically Erasable Programmable ROM), an HDD (Hard Disk Drive) and the like, for example. In the storage 15, the system programs and application programs, which are to be executed by the CPU 11, data necessary to execute the programs, and the like are stored. Also, in the storage 15, training history information is stored in which a training type determined by training determination processing (which will be described later; refer to FIG. 4) and a date and a running distance at the time when the training has been performed are associated.

The communication unit 1 (the transmission unit) 16 is configured to receive the exercise data generated when the running training has been performed from the measurement and recording device 20 or to transmit the training history information stored in the storage 15 to an external device separate from the training determination device 10 and the measurement and recording device 20, and is a communication unit adopting wireless standards such as Bluetooth (registered trademark) or a wired communication unit such as a USB terminal.

Measurement and Recording Devices

Figure 3B:
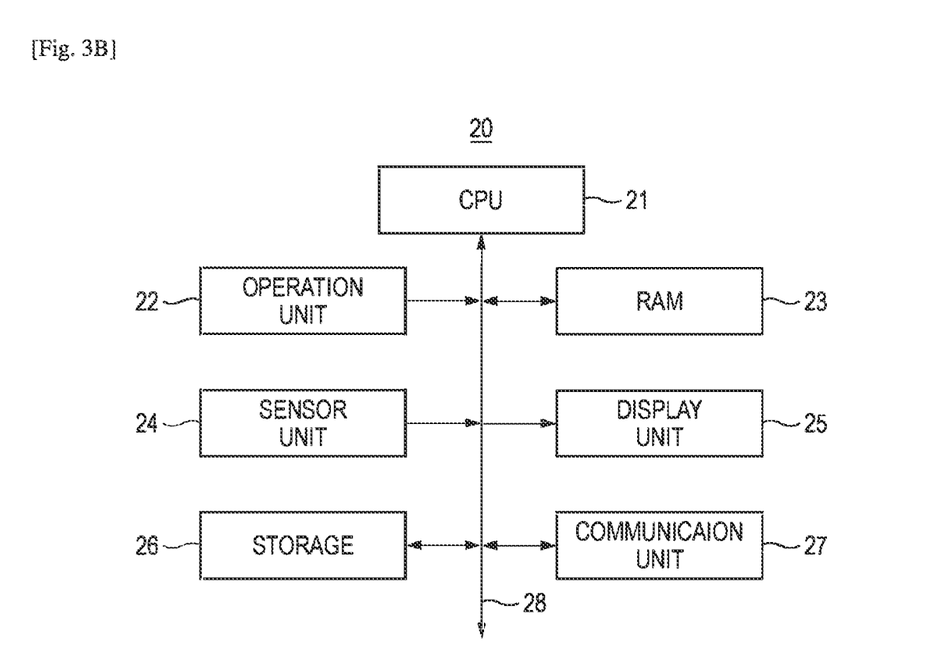
FIG. 3B is a block diagram depicting a functional configuration of the measurement and recording device.

Subsequently, an internal functional configuration of the measurement and recording device 20 is described with reference to FIG. 3B. FIG. 3B is a block diagram depicting a functional configuration of the measurement and recording device 20.

As shown in FIG. 3B, the measurement find recording device 20 includes a CPU 21, an operation unit 22, a RAM 23, a sensor unit 24, a display unit 25, a storage 26, and a communication unit 21. The respective units of the measurement and recording device 20 are connected via a bus 28.

The CPU 21 is configured to control the respective units of the measurement and recording device 20. The CPU 21 is configured to read a designated program of system programs and application programs stored in the storage 26, and to develop the read program on the RAM 23, thereby executing a variety of processing in cooperation with the program.

The operation unit 22 includes a power supply button (not shown) for switching on and off states of a power supply, a start/stop button (not shown) for instructing start/stop of data acquisition, and the like. Based on an instruction from the operation unit 22, the CPU 21 controls the respective units.

The RAM 23 is a volatile memory, and forms a work area in which diverse data and programs are temporarily stored.

The sensor unit 24 includes motion sensors capable of detecting motion of the measurement and recording device 20, such as a three-axis acceleration sensor, a gyro sensor, an earth magnetic sensor, and the like, and a GPS receiver capable of acquiring position information of the measurement and recording device 20, and is configured to output a measurement result to the CPU 21.

The display unit 25 is a display unit configured by a plurality of LED lamps and capable of displaying a transmission state of data (for example, whether data is being transmitted), on and off states of the GPS receiver, and the like.

The storage 26 is configured by a flash memory, an EEPROM and the like. In the storage 26, the system programs and application programs, which are to be executed by the CPU 21, data necessary to execute the programs, and die like are stored. Also, in the storage 26, the exercise data (for example, information such as a lap time and a running distance) generated when the running training has been performed is stored.

The communication unit 27 is configured to transmit the exercise data generated when the running training has been performed to the training determination device 10 under control of the CPU 21, and is a communication unit adopting wireless standards such as Bluetooth (registered trademark) or a wired communication unit such as a USB terminal.

Training Determination Processing

Figure 4:
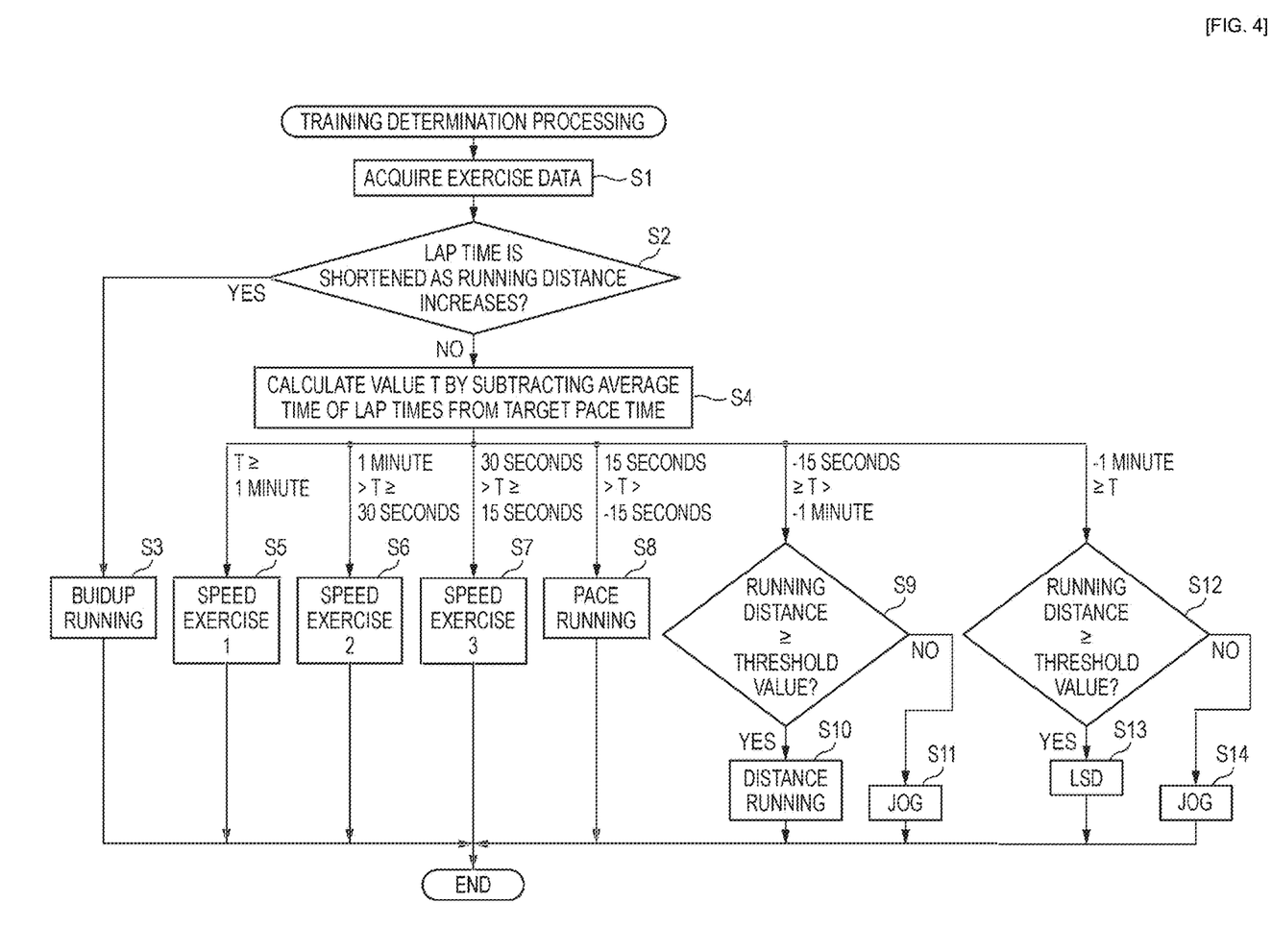
FIG. 4 is a flowchart depicting training determination processing.

Subsequently, training determination processing that is to be executed by the training determination device 10 is described with reference to FIG. 4. FIG. 4 is a flowchart depicting the training determination processing.

As shown in FIG. 4, the CPU 11 of the training determination device 10 first acquires the exercise data from the measurement and recording device 20 via the communication unit 16 (step S1).

Next, the CPU 11 determines whether each lap time is shortened as the running distance increases, based on the exercise data (step S2).

In the determination processing of step S2, when one lap lime is equal to previous lap time, the CPU 11 determines that the one lap time is shorter than the previous lap time. Also, in the determination processing of step S2, the CPU 11 performs the determination while excluding lap time of final 1 km during the running training. Also, in the determination processing of step S2, the CPU 11 performs the determination only when the running distance during the running training is equal to or longer than a pre- determined distance (for example, 4 km). That is, when the running distance during the running training is shorter than the predetermined distance, the CPU 11 determines that each lap time has not been shortened as the running distance increases (step S2; NO), and proceeds to processing of step S4.

When it is determined in step S2 that each lap time has been shortened as the running distance increases (step S2; YES), the CPU 11 determines that the type of the running training is "buildup running" (step S3), and ends the training determination processing. Herein, the CPU 11 stores the determined type, of the running training in the storage 15, as the training history information. Even after the training type is determined in each processing of step S5 to step S8, step S10, step S11, step S13 and step S14, which will be described later, the determined type of the running training is stored in the storage 15, as the training history information.

Meanwhile, in the training history information, the determined type of the running training and time information and running distance during the training, may be associated. As the time information, a date, time, a time period for which the training has been performed, and the like may be exemplified.

Also, when it is determined in step S2 that each lap time has, not been shortened as the running distance increases (step S52; NO), the CPU 11 calculates a value T by subtracting an average time of lap times from a target pace time (step S4). Herein, the target pace time means a standard pace time during training, and can be appropriately set and changed by the user. When it is not possible to acquire the average time of lap times in the processing of step S4, the CPU 11 may determine that the type of the running training is "others".

When the value T calculated in step S4 is a value equal to or greater than one minute (T≥1 minute), the CPU 11 determines that the type of the running training is "speed exercise 1" (step S5), and ends the training determination processing.

Also, when the value T calculated in step S4 is less than one minute and 30 seconds or greater (one minute>T≥30 seconds), the CPU 11 determines that the type of the running training is "speed exercise 2" (step S5), and ends the training determination processing.

Also, when the value T calculated in step S4 is less than 30 seconds and 15 seconds or greater (30 seconds>T≥15 seconds, the CPU 11 determines that the type of the running training is "speed exercise 3" (step S7), and ends the training determination processing.

Also, when the value T calculated in step S4 is less than 15 seconds and greater than 15 seconds (15>seconds>T>–15 seconds), the CPU 11 determines that the type of the running training is "pace running" (step S8), and ends the training determination processing.

Also, when the value T calculated in step S4 is 15 seconds or less and greater than –1 minute (–15 seconds≥T>–1 minute), the CPU 11 determines whether the running distance during the running training is equal to or greater than a predetermined threshold value (step S9). Herein, the predetermined threshold value is a threshold value set in correspondence to a value of a monthly target running distance set advance by the user. Specifically, for example, in a case in which the monthly target running distance is shorter than 100 km, the predetermined threshold value is set: to "10 km". Also, in a case in which the monthly target running distance is 100 km or longer, which is shorter than 200 km, the predetermined threshold value is set to "20 km".

Also, in a case in which the monthly target running distance is 200 km or longer and shorter than 300 km, the predetermined threshold value is set to "25 km" Also, in a case in which the monthly target running distance is 300 km or longer, the predetermined threshold value is set to "30 km".

When it is determined in step SO that the running distance during the running training is equal to or greater than the predetermined threshold value (step S9; YES), the CPU 11 determines that the type of the running training is "distance running" (step S10), and ends the training determination processing.

On the other hand, when it is determined in step S9 that the running distance during the running training is not equal to or greater than the predetermined threshold value (step S9: NO), the CPU 11 determines that the type of the running training is "jogging" (step S11), and ends the training determination processing.

Also, when the value T calculated in step S4 is –1 minute or shorter (–1 minute≥T). the CPU 11 determines whether the running distance during the running training is equal to or greater than a predetermined threshold value (step S12), like the determination processing of step S9. Herein, the predetermined threshold value is a value corresponding to the value of tire monthly target running distance set in advance by the user.

When it is determined in step S12 the running distance during the running training is equal to or greater than the predetermined threshold value (step S12: YES), the CPU 11 determines that the type of the running training is "LSD (Long Slow Distance)" (step S13), and ends the training determination processing.

On the other hand, when it is determined in step S12 the running distance during the running training is not equal to or greater than tire predetermined threshold value (step S12; NO), the CPU 11 determines that tire type of the running training is "jogging" (step S14), and ends the training determination processing.

In this way, whenever the training determination processing is executed by the training determination device 10, the determined training type is stored in the storage 15, as the training history information.

In the case in which the determined type of the running training and the time information and running distance during the training are associated and stored as the training history information in the storage 15, the training determination device 10 calculates a cumulative total of the running distances in each of the training types. Specifically, the training determination device 10 performs first calculation of monthly calculating a cumulative total of the running distances in each of the training types and second calculation of calculating a cumulative total of the running distances in each of the training types within a predetermined time period.

In the below, it is assumed that the determined type of the running training and the time information and running distance during the training are associated and stored as the training history information in the storage 15, and a monthly cumulative total screen, an entire cumulative total screen and a breakdown detail screen, which are displayed on the display unit 14 of the training determination device 10, are described with reference to FIGS. 5 to 7. The monthly cumulative total screen is a screen that is displayed on the display unit 14 when the first calculation has been performed by die training determination device 10, and the entire cumulative total screen is a screen that is displayed on the display unit 14 when the second calculation has been performed by the training determination device 10. Also, the breakdown detail screen is a screen for displaying details of contents displayed on the monthly cumulative total screen or the entire cumulative total screen. The screens are displayed on the display unit 14 when a predetermined running application program is activated in the training determination device 10.

Monthly Cumulative Total Screen

Figure 5:
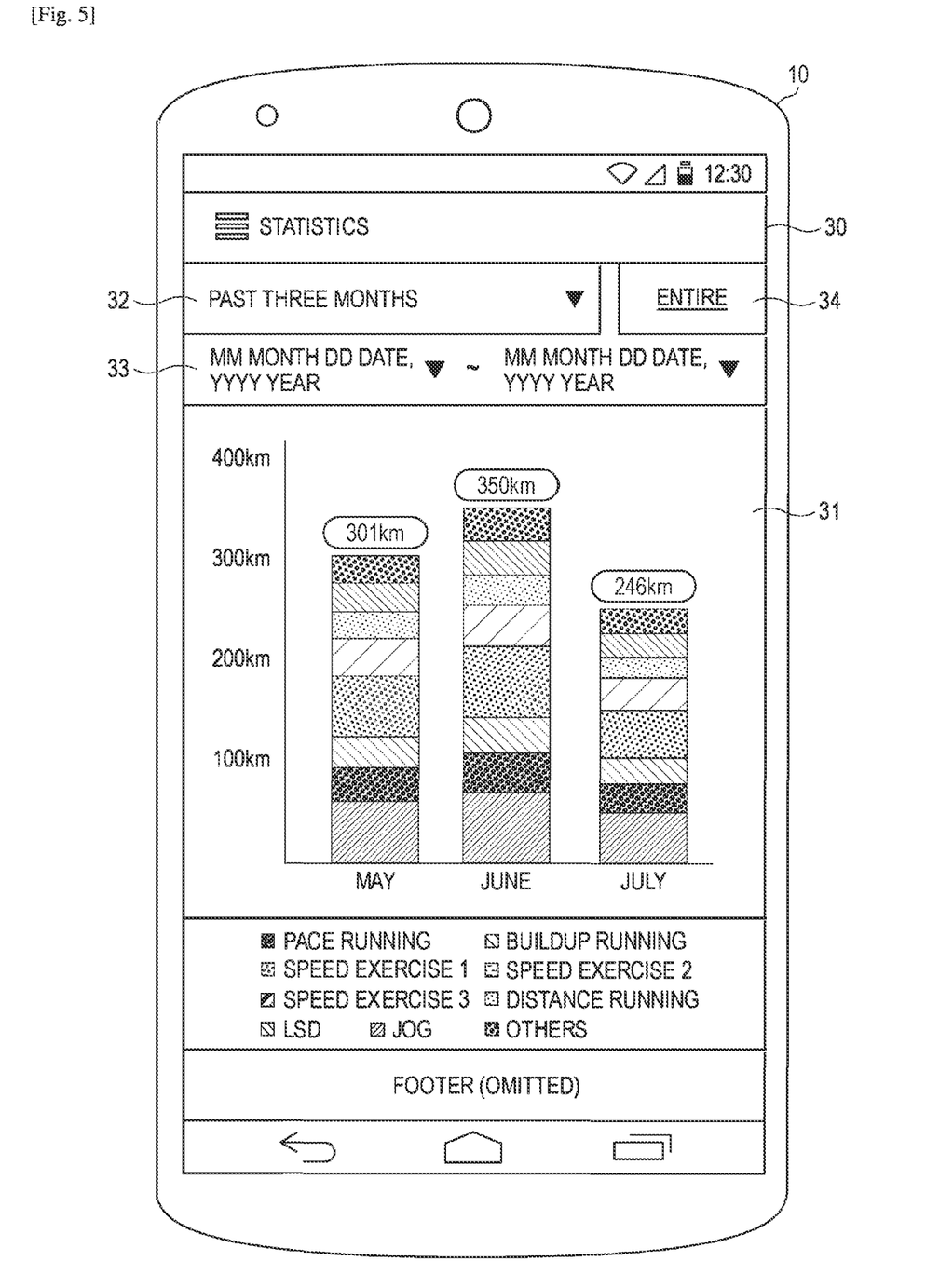
FIG. 5 depicts an example of a monthly cumulative total screen.

FIG. 5 depicts an example of the monthly cumulative total screen 30 that is to be displayed on the display unit 14 of the training determination device 10.

As shown in FIG. 5, the monthly cumulative total screen 30 includes a main display part 31, a range designation selection pan 32, a time period designation selection part 33, and an entire monthly selection part 34.

In the main display part 31, bar graphs in each of which cumulative totals of the running distances in each of the training types are stacked monthly are displayed. In the main display part 31, the bar graph of each month included in a range or time period selected by the range designation selection part 32 or the time period designation selection part 33 is displayed. Also, in the main display part 31, the bar graphs of up to six months can be displayed side by side, and when a range or time period selected by the range designation selection part 32 or the time period designation selection part 33 is 6 months or longer, the bar graph of each month included in the range or time period can be displayed by scroll.

The range designation selection part 32 is a so-called pull-down menu. When the user performs an input operation of selecting a button ▼ displayed in the range designation selection part 32, a menu (not shown) including "the past three years", "the past one year", "the past six months", "the past three months", "the past month" and "any time period", for example can be displayed. When an input operation of selecting a user's desired lime period (excluding "any time period") from the menu is performed, the bar graph of each month in the selected range (for example, "for the past three months") is displayed on the main display part 31. When an input operation of selecting "any time period" from the menu is performed, the time period designation selection part 33 is switched from an inactive state lo an active state, so that the user can perform an input operation on the time period designation selection part 33.

The time period designation selection part 33 is a selection part for designating any time period by a user setting, When the user performs an input operation of selecting a left button ▼ displayed in the time period designation selection part 33, a monthly calendar (not shown) can be displayed on the display unit 14, for example. When an input operation of selecting a user's desired date from the monthly calendar is performed, commencement of a time period can be designated. In the same manner, when the user performs an input operation of selecting a right button ▼ displayed the time period designation selection part 33, a monthly calendar (not shown) can be displayed on the display unit 14, for example.

When an input operation of selecting a user's desired date from the monthly calendar is performed, termination of the time period can be designated. When an input operation of designating user's desired commencement and termination from the time period designation selection part 33 is performed, the bar graph for each month in the designated time period can be displayed in the main display part 31.

The entire monthly selection part 34 is a so-called toggle button and enables the monthly cumulative total screen 30 displayed on the display unit 14 to be switched to an entire cumulative total screen 40, which will be described later, when the user performs an input operation of selecting a character part "entire" in the entire monthly selection part 34.

Entire Cumulative Total Screen

Figure 6:
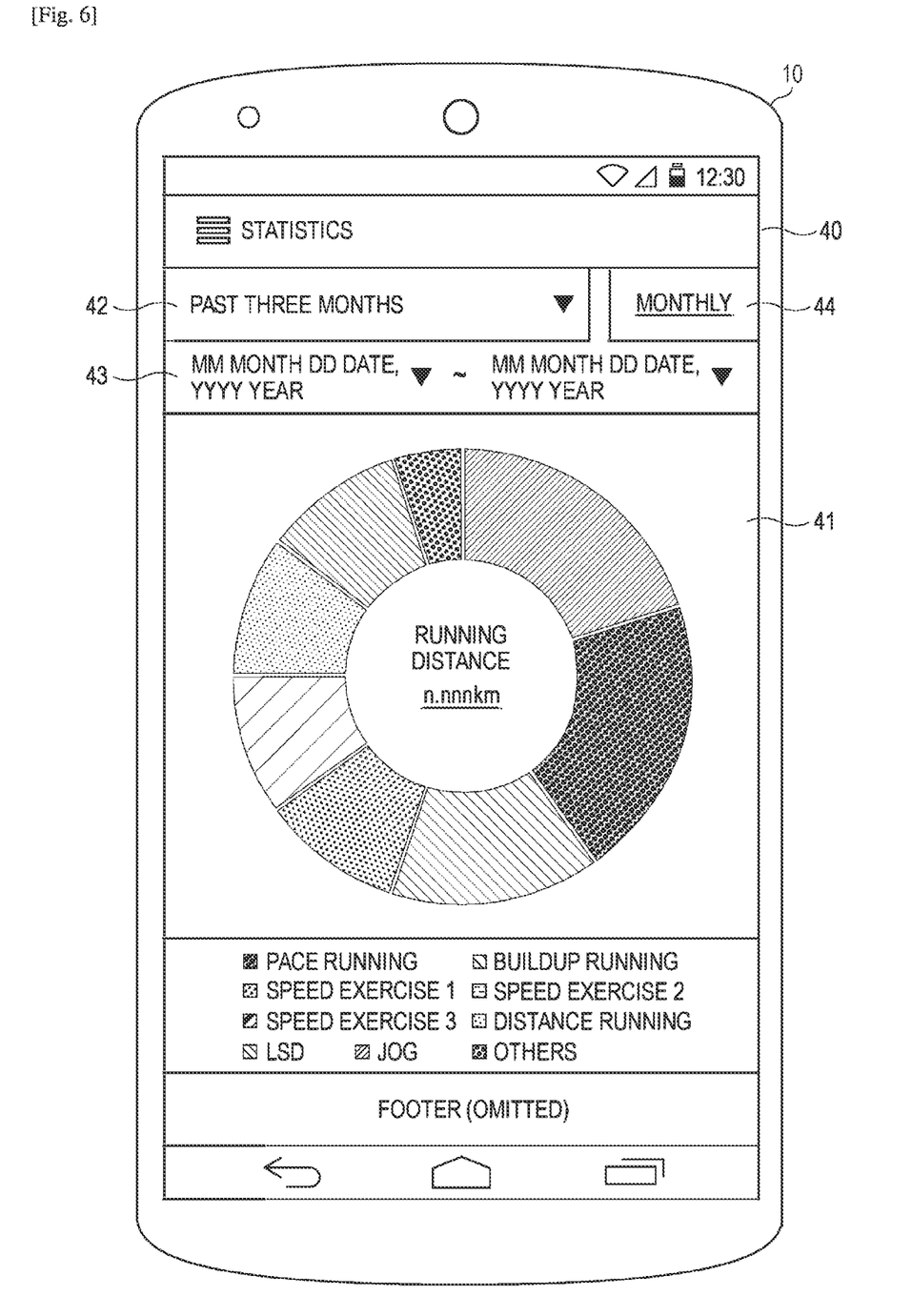
FIG. 6 depicts an example of an entire cumulative total screen.

FIG. 6 depicts an example of the entire cumulative total screen 40 that is to be displayed on the display unit 14 of the training determination device 10.

As shown in FIG. 6, the entire cumulative total screen 40 includes a main display part 41, a range designation selection part 42, a time period designation selection part 43, and an entire monthly selection part 44.

In the main display part 41, a circle graph, which indicates a ratio of a cumulative total of the running distances in each of the training types in a range or time period selected by the range designation selection part 42 or the time period designation selection part 43, is displayed. Also, a total running distance obtained by summing the cumulative totals of the running distances in each of the training types is displayed (which is displayed up to the third decimal place) in a center of the circle graph displayed in the main display part 41.

Since the range designation selection part 42 is a selection part having a similar function to the range designation selection part 32 to be displayed in the monthly cumulative total screen 30, the description thereof is omitted. Also, since the time period designation selection part 43 is a selection part having a similar function to the time period designation selection part 33 displayed in the monthly cumulative total screen 30, the description thereof is omitted.

The entire monthly selection part 44 is a so-called toggle button, and enables the entire cumulative total screen 40 displayed on the display unit 14 to be switched to the monthly cumulative total screen 30, when the user performs an input operation of selecting a character part "monthly" in the entire monthly selection part 44.

Breakdown Detail Screen

Figure 7:
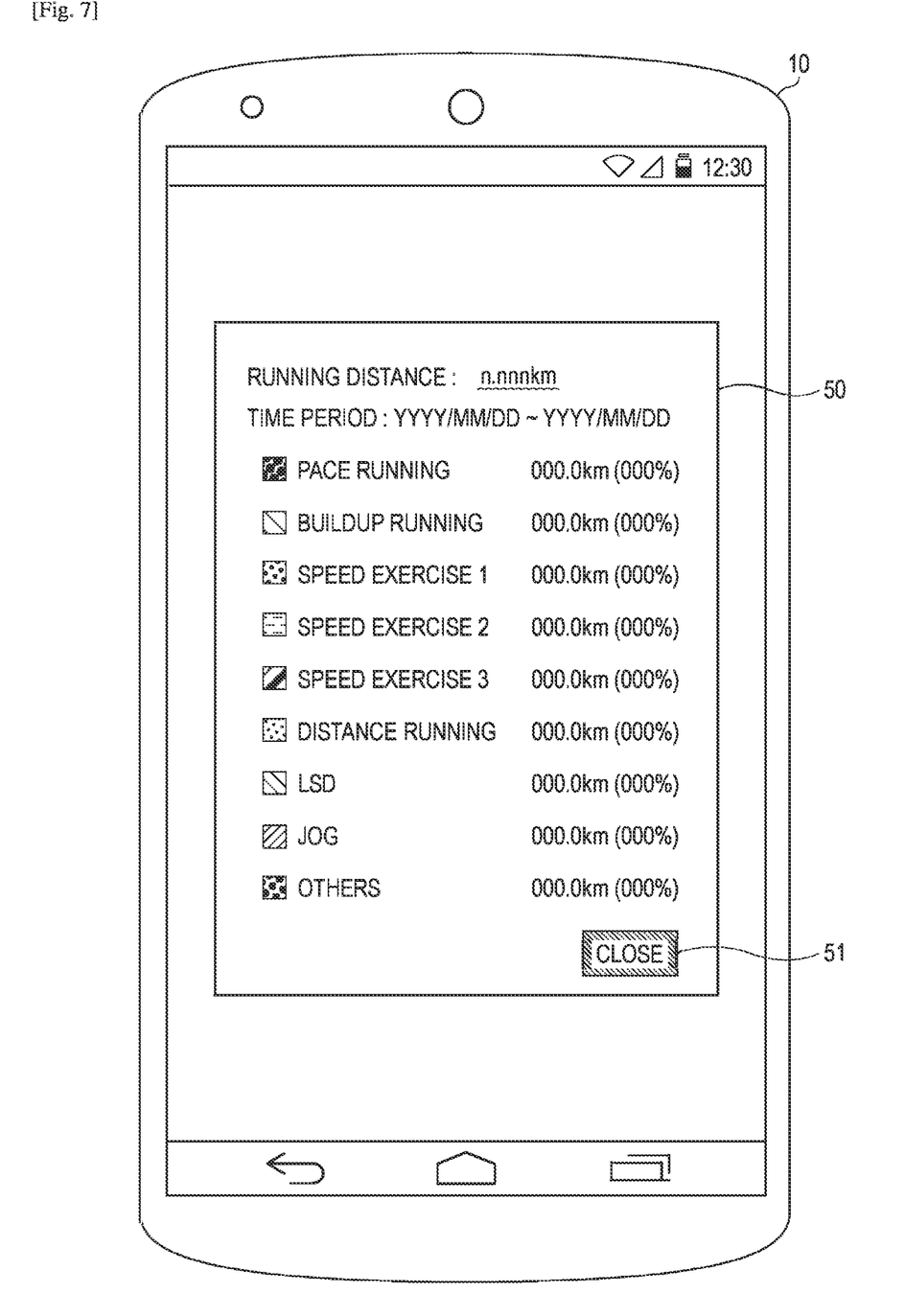
FIG. 7 depicts an example of a breakdown detail screen.

FIG. 7 depicts an example of a breakdown detail screen 50 that is to be displayed on the display unit 14 of the training determination device 10.

The breakdown detail screen 50 is a screen that is displayed on the display unit 14 when the user performs an input operation of selecting the bar graph displayed in the main display part 31 of the monthly cumulative total screen 30 shown in FIG. 5 or an input operation of selecting the circle graph displayed in the main display part 41 of the entire cumulative total screen 40 shown in FIG. 6, for example.

Specifically, when the user performs the input operation of selecting the bar graph of July displayed in the main display part 31 of the monthly cumulative total screen 30 shown in FIG. 5, for example, a cumulative total of the running distances in each of the training types of July and a ratio of the cumulative total to the total running distance are displayed in the breakdown detail screen 50. Also, when the user performs the input operation of selecting the circle graph displayed in the main display part 41 of the entire cumulative total screen 40 shown in FIG. 6, for example, a cumulative total of the running distances in each of the training types and a ratio of the cumulative total to the total running distance in the range or time period selected with the range designation selection part 42 or the lime period designation selection part 43 are displayed in the breakdown detail screen 50.

Also, a close button 51 is displayed in the breakdown detail screen 50, so that when the user performs an input operation of selecting the close button 51, the breakdown detail screen is returned to the original screen (the monthly cumulative total screen 30 or the entire cumulative total screen 40).

As described above, according to the exemplary embodiment, the training determination device 10 acquires the exercise data generated when the user has performed the running training, and determines the training type (LSSD (Long Slow Distance), jogging, distant running, pace running, speed exercise, buildup running, and others), based on the exercise data. Therefore, according to the training determination device 10, since it is possible to determine the training type whenever the running training is performed, it is possible to efficiently perform the running training, based on a result of the determination.

Specifically, when each lap time of the lap time information is equal to or shorter than a previous lap time of each lap time, the training determination device 10 determines that the training type is the buildup running. Therefore, it is possible to correctly determine the buildup running.

Also, when at least one lap time of the respective lap times is longer than the previous lap time and the average time of the respective lap times is longer than the target pace time by 15 seconds (first time) or greater, the training determination device 10 determines that the training type is the speed exercise. Therefore, it is possible to correctly determine the speed exercise.

Also, when the average time of the respective lap times is longer than the target pace time by 15 seconds (first time) or greater, the training determination device 10 further determines one speed exercise from the plurality of types of speed exercises 1 to 3, in correspondence to the average time of the respective lap times. Therefore, it is possible to correctly determine the speed exercises 1 to 3, in correspondence to the average time of the respective lap times.

Also, when an absolute value of the value obtained by subtracting the average time of the respective lap times from the target pace time is smaller than the value of 15 seconds (first time), the training determination device 10 determines that the training type is the pace running. Therefore, it is possible to correctly determine the pace running.

Also, when the average time of the respective lap times is slower than the target pace time by 15 seconds (first time) or greater and the value of the running distance is smaller than the predetermined threshold value, the training determination device 10 determines that the training type is the jogging. Therefore, it is possible to correctly determine the jogging.

Also, when the average time of the respective lap times is slower than the target pace time by 60 seconds (second time) or greater, which is longer than 15 seconds (first time), and the value of the running distance is equal to or greater than the predetermined threshold value, the training determination device 10 determines that the training type is the LSD. Therefore, it is possible to correctly determine the LSD.

Also, when the value obtained by subtracting the average time of the respective lap times from the target pace time is a negative value, an absolute value thereof is a value of 15 seconds (first time) or greater and smaller than 60 seconds (second time) and the value of the running distance is equal to or greater than the predetermined threshold value, the training determination device 10 determines that the training type is the distance running. Therefore, it is possible to correctly determine the distance running.

Also, since the training determination device 10 sets the predetermined threshold value, in correspondence to the monthly target running distance (the target running distance in the predetermined lime period) set by the user, it is possible to correctly determine each of the jogging, the USD and the distance running, respectively, in accordance with the running level of the user.

Also, since the training determination device 10 calculates the cumulative total of the running distances in each of the training types, based on the training history information in which the determined training type and the running distance during the training are associated, it is possible to perceive an amount of exercise during each training. Thereby, it is possible to use the amount of exercise by reference when planning a next training and thereafter. Also, if is possible to use the amount of exercise by reference when analyzing whether the performed training is good or bad from a race result of competitions and the like.

Also, since the training determination device 10 stores the determined training type in the storage 15, as the training history information, it is possible to perceive the training type in each training performed in the past, so that if is possible to perform the running training more efficiently.

Also, since the training determination device 10 stores the training history information, in which the determined training type and the time information and running distance during the training are associated, in the storage 15, it is also possible to perceive the time information and running distance during the training, in addition to the training type of each training performed in the past, so that it is possible to perform the running training further efficiently.

Also, since the training determination device 10 calculates the cumulative total of the running distances in each of the training types, based on the training history information stored in the storage 15, it is possible to perceive the cumulative total of the running distances in each of the training types, so that it is possible to perform the running training further efficiently.

Also, since the training determination device 10 performs the first calculation of monthly calculating the cumulative total of the running distances in each of the training types and the second calculation of calculating the cumulative total of the running distances in each of the training types within the predetermined time period, it is possible to perceive the amount of exercise in each of the training types for each of diverse time periods, so that it is possible to perform the running training further efficiently.

Also, the training determination device 10 can designate the predetermined time period, based on the user operation. Specifically, since the training determination device 10 can designate, as the predetermined time period, any one of the past three years, past one year, the past six months, the past three months, the past month, and any time period set by the user setting, it is possible to perceive the amount of exercise in each of the training types for the users desire time period, so that it is possible to perform the running training further efficiently.

Also, since the training determination device 10 displays the calculated cumulative total of the running distances in each of the training types on the display unit 14, it is possible to visually perceive the amount of exercise in each of the training types.

Also, when displaying the cumulative total obtained by the first calculation on the display unit 14, the training determination device 10 displays the bar graph in which the cumulative totals of the running distances in each of the training types are stacked monthly, and when displaying the cumulative total obtained by the second calculation on the display unit 14, the training determination device displays the circle graph, which indicates the ratios of the cumulative totals of the mining distances in each of the training types in the predetermined time period. Therefore, it is possible to easily perceive the amount cat exercise in each training, in accordance with modes of calculation.

Also, when displaying the cumulative total obtained by the second calculation on the display unit 14 with the circle graph, the training determination device 10 displays the total distance, too, which is obtained by summing the cumulative totals of the running distances in each of the training types in the predetermined time period, on the display unit 14. Therefore, it is possible to easily perceive the amount at exercise in each of the training types in the predetermined time period from the total running distance.

Also, since the training determination device 10 can transmit the training history information stored in the storage 15 to art external device separate from the training determination device 10, it is possible to perceive the training type in each training performed in the past also in the separate external device.

Although the exemplary embodiment of the present invention has been described, the present invention is not limited to the exemplary embodiment and a variety of modifications can be made without departing from the gist thereof.

For example, in the exemplary embodiment, when the user has performed the running training, the training determination device 10 determines the training, type by using the exercise data of the user acquired from the measurement and recording device 20. However, the training determination device 10 may be provided with a similar function to the measurement and recording device 20, so that the training determination device 10 may directly measure the exercise data of the user and determine. the training type by using the measured exercise data when the user has performed the running training.

Also, in the exemplary embodiment, the training determination device 10 includes the display unit and displays the monthly cumulative total screen 30, the entire cumulative total screen 40, and the breakdown detail screen 50 on the display unit 14. However, the determined training type and training history information stored in the training determination device 10 may be transmitted to an external device separate from the training determination device 10 and the measurement and recording device 20 by the communication unit 16, and the determined training type and training history information may be displayed on the external device.

Also, in the exemplary embodiment, each lap time as the exercise data is a lap time per 1 km. However, the running distance, which is a basis when measuring the lap time, is not limited to 1 km. For example, lap time per 400 m may be used, and any distance may be set by the user.

Although the exemplary embodiment of the present invention has been described, the scope of the present invention is not limited to the exemplary embodiment, and includes the scope of the invention defined in tint claims and equivalents thereto.

This application is based on Japanese Patent Application No. 2018-237023 filed on Dec. 19, 2018, the entire subject matter of which is incorporated herein by reference.

The invention claimed is:

1. A running training system for a user who trains by running laps, the running training system comprising:
   a measurement and recording device configured for being worn by a user during running trainings and for obtaining and transmitting data related to the running trainings, the data including lap times and running distance;
   at least one sensor of the measurement and recording device configured for detecting motion and acquiring position information of the measurement and recording device for generating the data related to the running trainings;
   a training determination device configured for receiving the data from the measurement and recording device;
   a processor of the training determination device that, based on the lap times and the distances run, is configured to determine types of running training performed by the user, wherein speed running training is determined as one of the types of running training when at least one lap time of one of a plurality of laps run during a running training is longer than a previous lap time of another one of the plurality of laps run during the running training, and when an average lap time of the plurality of laps run during the running training is less than a predetermined target pace time by a first time or greater, the processor being further configured determine different levels of speed running trainings based on an amount of time that the average time is less than the predetermined target pace time; and
   a user input of the training determination device that allows the user to enter and vary the target pace time which is used in the determination of the different levels of speed running trainings so that the determination of the different levels of speed running trainings by the processor can be personalized by the user.

2. The running training system according to claim 1, wherein the types of running training that the processor is configured to determine includes at least one of LSD (Long Slow Distance) running training, jogging running training, distance running training, pace running training, and buildup running training, in addition to the speed running training.

3. The running training system according to claim 2, wherein
   when each lap time is equal to or shorter than a previous lap time during a running training, the processor is configured to determine that the type of running training is buildup running training.

4. The running training system according to claim 2, wherein
   when an absolute value of a value obtained by subtracting the average time of the respective lap times from the predetermined target pace time is smaller than a value of the first time during a running training, the processor is configured to determine that the type of running training is pace running training.

5. The running training system according to any one of claim 2, wherein
   when the average time of the respective lap times is longer than the predetermined target pace time by the first time or greater and a value of the running distance is smaller than a predetermined threshold value during a running training, the processor is configured to determine that the running training type is jogging running training.

6. The running training system according to claim 5,
wherein the processor is configured to determine a value of the predetermined threshold value that is based on and is less than a target running distance in a predetermined time period with the user input allowing the user to enter and vary the target running distance so that the determination of jogging running training can be personalized by the user.

7. The running training system according to claim 2, wherein
when the average time of the respective lap times is longer than the predetermined target pace time by a second time, which is longer than the first time, or greater, and the value of the running distance is equal to or greater than a predetermined threshold value during a running training, the processor is configured to determine that the running training type is LSD running training.

8. The running training system according to claim 7,
wherein the processor is configured to determine a value of the predetermined threshold value that is based on and is less than a target running distance in a predetermined time period with the user input allowing the user to enter and vary the target running distance so that the determination of LSD running training can be personalized by the user.

9. The running training system according to claim 2, wherein
when a value obtained by subtracting the average time of the respective lap times from the predetermined target pace time is a negative value, an absolute value thereof is equal to or greater than a value of the first time and is smaller than a value of a second time, which is longer than the first time, and the value of the running distance is equal to or greater than a predetermined threshold value during a running training, the processor is configured to determine that the running training type is distance running training.

10. The running training system according to claim 9,
wherein the processor is configured to determine a value of the predetermined threshold value that is based on and is less than a target running distance in a predetermined time period with the user input allowing the user to enter and vary the target running distance so that the determination of distance running training can be personalized by the user.

11. The running training system according to claim 2,
wherein the memory is configured to store training history information in which the running training type determined by the processor is associated with time information for running trainings performed training and running distances during the performed running trainings, and
the processor is configured to perform at least two types of different calculations for a cumulative total of the running distance for each running training type, based on the training history information stored by the memory.

12. The running training system according to claim 11, wherein the processor is configured to perform
a first calculation for monthly calculating a cumulative total of a running distance in each training type and a second calculation for calculating a cumulative total of the running distance in each training type in a predetermined time period.

13. The running training system according to claim 12, wherein the user input allows the user to enter the predetermined time period.

14. The running training system according to claim 12, wherein
the processor is configured to allow the user to enter via the user input, as the predetermined time period, one of past three years, past one year, past six months, past three months, past one month, and any time period set by the user.

15. The running training system according to claim 12, wherein
the training determination device includes a display;
the processor is configured to display on the display the cumulative total of the running distance calculated in each running training type, and
when displaying on the display a monthly cumulative total screen which comprises the cumulative total obtained by the first calculation, a display controller is configured to display on the display a bar graph in which cumulative totals of running distances in the respective running training types are stacked monthly,
when displaying on the display an entire cumulative total screen which comprises the cumulative total obtained by the second calculation, the display controller is configured to display on the display a circle graph which represents ratios of the cumulative totals of the running distances in the respective running training types in the predetermined time period,
when displaying on the display the cumulative total obtained by the second calculation with the circle graph, the processor is configured to additionally display on the display showing the entire cumulative total screen a total running distance which is obtained by summing the cumulative totals of the running distances in each of the running training types in the predetermined time period, the user input allows a user to select either the monthly cumulative total screen or the entire cumulative total screen to be displayed on the display so as to allow for ease of switching between the display of the monthly cumulative total screen and the entire cumulative total screen on the display.

16. The running training system according to claim 11, wherein the processor is configured to transmit the training history information stored in the memory to an external device separate from the training determination device.

17. The running training system according to claim 1 wherein the different types of running training include distance running training that is determined by the processor when speed running training is not determined and the distance run in the running training is equal to or greater than a predetermined threshold value that is based on and is less than a target running distance in a predetermined time period, and the user input unit allows the user to enter and vary the target running distance so that the determination of distance training by the processor can be personalized by the user.

18. The running training system according to claim 1 further comprising a memory that stores running training history information including, for each running training, the determined type of running training and the lap times and the running distance, and a display of the training determination device that allows the user to view the running distances of the different types of running training completed for personalizing distance amounts of future running trainings for each of the running training types.

* * * * *

UNITED STATES PATENT AND TRADEMARK OFFICE
CERTIFICATE OF CORRECTION

PATENT NO. : 12,263,392 B2  
APPLICATION NO. : 17/415658  
DATED : April 1, 2025  
INVENTOR(S) : Nishizaka et al.

Page 1 of 1

It is certified that error appears in the above-identified patent and that said Letters Patent is hereby corrected as shown below:

In the Claims

In Column 12, Claim 5, Line 60, delete "to any one of" and insert -- to --, therefor.

In Column 13, Claim 11, Line 50, delete "performed training" and insert -- performed --, therefor.

In Column 14, Claim 17, Line 46, delete "claim 1" and insert -- claim 1, --, therefor.

In Column 14, Claim 18, Line 57, delete "claim 1" and insert -- claim 1, --, therefor.

Signed and Sealed this  
Fourth Day of November, 2025

John A. Squires  
*Director of the United States Patent and Trademark Office*